(12) United States Patent
White et al.

(10) Patent No.: US 9,703,751 B2
(45) Date of Patent: Jul. 11, 2017

(54) APPARATUS AND SENSORS FOR ATTACHMENT TO THE APPARATUS

(71) Applicant: Nokia Corporation, Espoo (FI)

(72) Inventors: Richard White, Huntingdon (GB); Michael Robert Astley, Cambridgeshire (GB); Stefano Marco Borini, Cambridgeshire (GB)

(73) Assignee: Nokia Technologies Oy, Espoo (FI)

( * ) Notice: Subject to any disclaimer, the term of this patent is extended or adjusted under 35 U.S.C. 154(b) by 912 days.

(21) Appl. No.: 13/670,856

(22) Filed: Nov. 7, 2012

(65) Prior Publication Data
US 2014/0129174 A1 May 8, 2014

(51) Int. Cl.
| | |
|---|---|
| *G01D 1/00* | (2006.01) |
| *G06F 15/00* | (2006.01) |
| *A61B 5/0205* | (2006.01) |
| *H05K 13/00* | (2006.01) |
| *A61B 5/00* | (2006.01) |
| *G06F 1/16* | (2006.01) |

(52) U.S. Cl.
CPC ............ *G06F 15/00* (2013.01); *A61B 5/0024* (2013.01); *A61B 5/0205* (2013.01); *A61B 5/681* (2013.01); *A61B 5/6831* (2013.01); *A61B 5/0002* (2013.01); *A61B 5/443* (2013.01); *A61B 5/6824* (2013.01); *A61B 2560/0443* (2013.01); *A61B 2562/0214* (2013.01); *A61B 2562/043* (2013.01); *A61B 2562/063* (2013.01); *G06F 1/163* (2013.01); *H05K 13/0023* (2013.01); *Y10T 29/49018* (2015.01)

(58) Field of Classification Search
USPC ........................................................ 702/127
See application file for complete search history.

(56) References Cited

U.S. PATENT DOCUMENTS

| | | | | |
|---|---|---|---|---|
| 5,104,623 A | * | 4/1992 | Miller ........................ | 422/82.06 |
| 5,551,437 A | * | 9/1996 | Lotscher ...................... | 600/485 |
| 6,206,835 B1 | | 3/2001 | Spillman, Jr. et al. ....... | 600/485 |
| 6,238,354 B1 | * | 5/2001 | Alvarez ....................... | 600/549 |
| 7,680,523 B2 | | 3/2010 | Rytky .......................... | 600/388 |

(Continued)

FOREIGN PATENT DOCUMENTS

| | | |
|---|---|---|
| CN | 101108125 A | 1/2008 |
| WO | WO-2008/035993 A1 | 3/2008 |

OTHER PUBLICATIONS

"Disposable Wireless Sensors", Atlas Technology, http://www.atlastechnology.co.uk/index.php?p=1_112; 2013, 2 pgs.
"Worlds first disposable Wireless Devices", Atlas Technology, http://www.atlastechnology.co.uk/index.php?/news&nid=21; 2009, 1 pg.
"NFC Cell Phone Sensor Networks", GENTAG Technology, http://www.gentag.com/technology.html; 2013, 2 pgs.

(Continued)

*Primary Examiner* — Paul D Lee
(74) *Attorney, Agent, or Firm* — Harrington & Smith (57) ABSTRACT

An apparatus and plurality of sensors where the apparatus includes a plurality of coupling elements; a plurality of attachment portions configured to enable a plurality of sensors to be removably attached to the apparatus; at least one processor; and at least one memory including computer program instructions; wherein the at least one memory and the computer program instructions are configured to, with the at least one processor, enable the apparatus to individually address each of the plurality of coupling elements to obtain a reading from each of the plurality of sensors attached to the apparatus.

20 Claims, 6 Drawing Sheets

(56) References Cited

U.S. PATENT DOCUMENTS

| | | | |
|---|---|---|---|
| 2001/0043514 A1 | 11/2001 | Kita | 368/281 |
| 2002/0180605 A1* | 12/2002 | Ozguz et al. | 340/573.1 |
| 2003/0018673 A1 | 1/2003 | Maier et al. | 708/206 |
| 2007/0279852 A1 | 12/2007 | Daniel et al. | 361/683 |
| 2008/0114220 A1 | 5/2008 | Banet et al. | 600/301 |
| 2008/0208030 A1 | 8/2008 | Finneran et al. | 600/393 |
| 2008/0287769 A1 | 11/2008 | Kurzweil et al. | 600/388 |
| 2009/0318793 A1 | 12/2009 | Datta et al. | 600/391 |
| 2010/0145317 A1* | 6/2010 | Laster | A61B 5/0031 604/891.1 |
| 2010/0201542 A1 | 8/2010 | Harnett | 340/870.28 |
| 2010/0298687 A1 | 11/2010 | Yoo et al. | 600/391 |
| 2012/0024889 A1 | 2/2012 | Robertson et al. | 222/23 |

OTHER PUBLICATIONS

"Gartner Names Cisco a Leader in Web Conferencing", InformationWeek, http://www.informationweek.com/healthcare/mobile-wireless/10-wearable-devices-to-keep- . . . ; 2013, 1 pg.

"Wearable devices track people via wireless network", http://usatoday30.usatoday.com/tech/news/story/2012-04-30/wireless-track-patients/546484 . . . ; Apr. 30, 2012, 3 pgs.

"Outsourcing Engineering Services to India", Engineering Services Outsourcing, http://www.engineeringservicesoutsourcing.com/ref/eng/fut/uni/wearable_devices.html; 2006, 4 pgs.

"Wearable Sensor Gathers Physiological Data for Up to a Week", Brian Klein, MedGadget, http://www.medgadget.com/2012/03/wearable-sensor-gathers-physiological-data-for-up-to- . . . ; Mar. 16, 2012, 4 pgs.

"The World's Smartest Training App Just Got Smarter", Polar Global, http://www.polar.com/en/; 2013, 2 pgs.

* cited by examiner

APPARATUS AND SENSORS FOR ATTACHMENT TO THE APPARATUS

TECHNOLOGICAL FIELD

Embodiments of the present invention relate to an apparatus and sensors for attachment to the apparatus. In particular, they relate to an apparatus and sensors for attachment to the apparatus in which a plurality of user replaceable sensors may be attached to an apparatus.

BACKGROUND

Sensors such as wearable sensors are known. The sensors may be used for applications such as monitoring health, monitoring activity of a user, monitoring an environment of a user or monitoring a context of a user or any other suitable parameters which may be monitored.

It is useful to provide sensors which may be part of a system which is easy and convenient for a user to use.

BRIEF SUMMARY

According to various, but not necessarily all, examples of the disclosure there may be provided an apparatus comprising: a plurality of coupling elements; a plurality of attachment portions configured to enable a plurality of sensors to be removably attached to the apparatus; at least one processor; and at least one memory including computer program instructions; wherein the at least one memory and the computer program instructions are configured to, with the at least one processor, enable the apparatus to individually address each of the plurality of coupling elements to obtain a reading from each of the plurality of sensors attached to the apparatus.

In some examples each of the plurality of coupling elements may be identical.

In some examples the coupling elements may comprise an antenna.

In some examples the plurality of attachment portions may be configured to enable a user of the apparatus to remove and replace the plurality of sensors.

In some examples the plurality of attachment portions may be configured so that the separation between the sensor and the antenna is the same for each pairing of sensor and antenna.

In some examples the plurality of attachment portions may be configured to enable a sensor to be positioned in close proximity to a coupling element.

In some examples the plurality of attachment portions may be configured to enable a sensor to be positioned close enough to the sensor to enable near field coupling between the sensor and the coupling element.

In some examples the plurality of attachment portions may comprise means for coupling to a corresponding attachment portion of a sensor.

In some examples the plurality of attachment portions may comprise a portion configured to receive an adhesive portion of a sensor.

In some examples the apparatus may be configured to be worn by a user.

In some examples the apparatus may comprise a strap configured to enable the apparatus to be attached to a user's body. The strap may be configured to enable the apparatus to be attached to a user's wrist. A first subset of the plurality of antennas may be provided on a first side of the strap and a second subset of the plurality of antennas may be provided on a second side of the strap. The apparatus may be configured so that when the apparatus is attached to a user the second subset of sensors is positioned to be adjacent to the skin of user.

In some examples the apparatus may comprise a communications module configured to enable the apparatus to communicate with another apparatus.

According to various, but not necessarily all, examples of the disclosure there may be provided a sensor configured to be attached to an apparatus as described above.

According to various, but not necessarily all, examples of the disclosure there may be provided a sensor comprising: a sensing portion; at least one coupling element; and an attachment portion configured to enable the sensor to be removably attached to an apparatus to enable the coupling element to transfer data to the apparatus.

In some examples the sensor portion may be configured to sense a parameter and to provide a signal indicative of the sensed parameter to the coupling element.

In some examples the coupling element may comprise an antenna.

In some examples the attachment portion may be configured to enable a user of an apparatus to removably attach the sensor to the apparatus.

In some examples the attachment portion may be configured to enable the sensor to be positioned in close proximity to a coupling element of an apparatus. In some examples the attachment portion may comprise an adhesive portion.

In some examples the sensor may further comprise an integrated circuit configured to encode data obtained from the sensor portion and provide the encoded data to the coupling element.

In some examples the sensor may comprise an alignment portion configured to enable a user to position the sensor on an apparatus. The alignment portion may comprise a visual indication. The alignment portion may comprise the shape of the sensor.

In some examples the sensor may comprise a visual indication of the sensed parameter.

According to various, but not necessarily all, examples of the disclosure there may be provided a method comprising: removably attaching at least one sensor to an apparatus wherein the apparatus comprises; a plurality of coupling elements; a plurality of attachment portions configured to enable the at least one sensor to be removably attached to the apparatus; at least one processor; and at least one memory including computer program instructions wherein the at least one memory and the computer program instructions are configured to, with the at least one processor, enable the apparatus to individually address a coupling element to obtain a reading from the at least one sensor attached to the apparatus; and the at least one sensor comprises a sensing portion; a sensing antenna; and an attachment portion configured to enable the sensor to be removably attached to the apparatus.

In some examples the apparatus may comprise an apparatus as described above. In some examples the sensor may comprise a sensor as described above.

According to various, but not necessarily all, examples of the disclosure there may be provided a method comprising: removing a first sensor from an apparatus and replacing the first sensor with a second sensor wherein the apparatus comprises; a plurality of coupling antennas; a plurality of attachment portions configured to enable the at least one sensor to be removably attached to the apparatus; at least one processor; and at least one memory including computer program instructions wherein the at least one memory and the computer program instructions are configured to, with the at least one processor, enable the apparatus to individually address a coupling element to obtain a reading from the at least one sensor attached to the apparatus; and the sensors comprise a sensing portion; a sensing coupling element; and an attachment portion configured to enable the sensors to be removably attached to the apparatus.

In some examples the first sensor may be configured to sense a different parameter to the second sensor.

In some examples the apparatus may comprise an apparatus as described above. In some examples the sensor may comprise a sensor as described above.

The apparatus may be for sensing. The apparatus may be for sensing parameters.

BRIEF DESCRIPTION

For a better understanding of various examples that are useful for understanding the brief description, reference will now be made by way of example only to the accompanying drawings in which.

DETAILED DESCRIPTION

The Figures illustrate an apparatus 1 comprising: a plurality of coupling elements 7; a plurality of attachment portions 13 configured to enable a plurality of sensors 2 to be removably attached to the apparatus 1; at least one processor 3; and at least one memory 5 including computer program instructions 11; wherein the at least one memory 5 and the computer program instructions 11 are configured to, with the at least one processor 3, enable the apparatus 1 to individually address each of the plurality of coupling elements 7 to obtain a reading from each of the plurality of sensors 2 attached to the apparatus 1.

Figure 1:
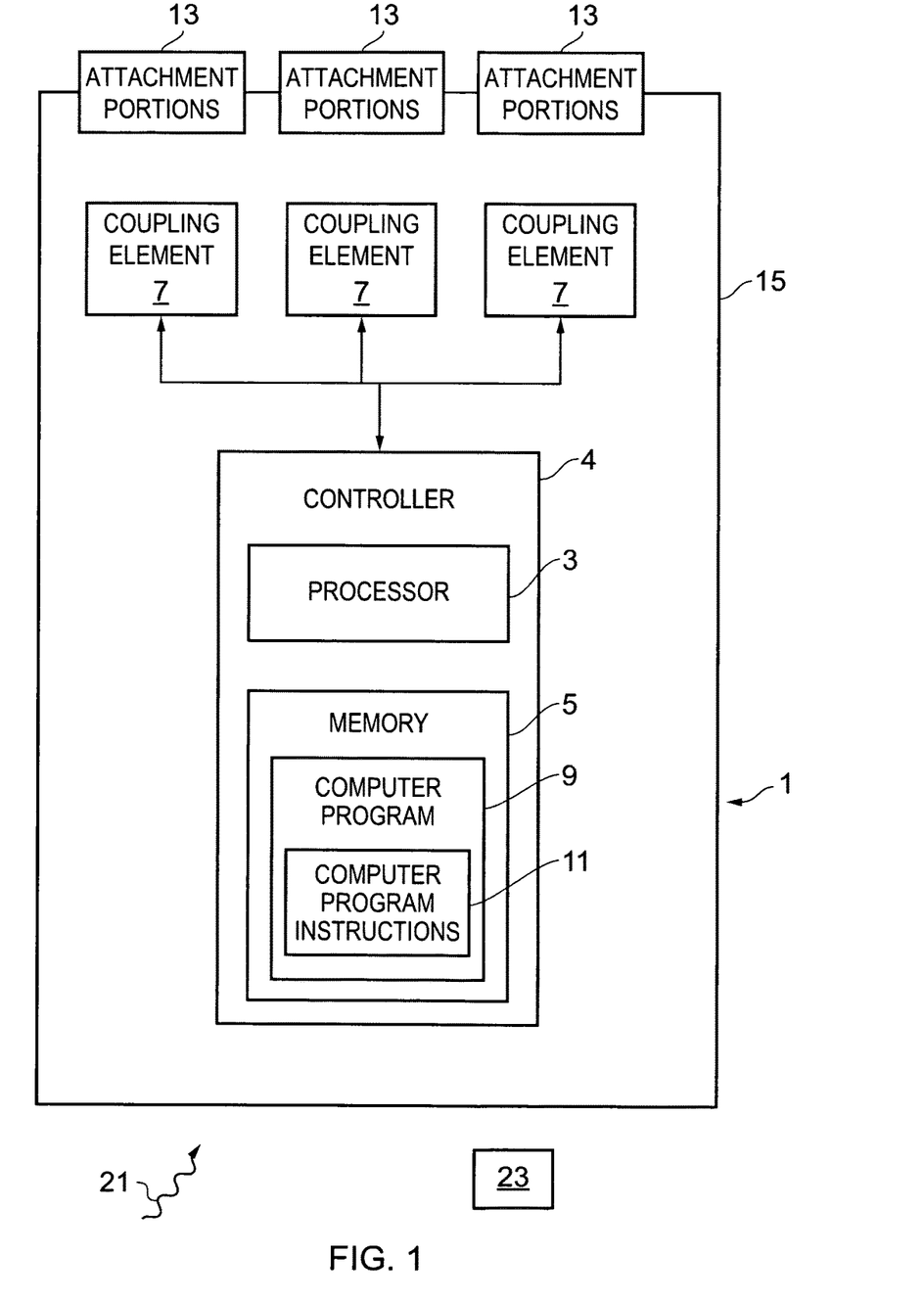
FIG. 1 illustrates an apparatus according to examples of the disclosure.

FIG. 1 illustrates an apparatus 1 according to examples of the disclosure. Only features referred to in the following description are illustrated in FIG. 1. However, it should be understood that the apparatus 1 may comprise additional features that are not illustrated. For example the apparatus 1 may comprise a communications module which may enable the apparatus 1 to communicate with another apparatus or within a wireless communication network.

The example apparatus 1 of FIG. 1 comprises a plurality of coupling elements 7 and a plurality of attachment portions 13. In the example of FIG. 1 three coupling elements 7 and three attachment portions 13 are illustrated. It is to be appreciated that any number of coupling elements 7 and attachment portions 13 may be provided in the various examples of the disclosure.

The attachment portions 13 may comprise any means which enables a plurality of sensors to be attached to the apparatus 1. The attachment portions 13 may be configured to couple to a corresponding portion of a sensor. Each of the plurality of attachment portions 13 may enable a sensor to be attached to the apparatus 1. The attachment portions 13 of the apparatus 1 may comprise receiving attachments portions.

The receiving attachment portions 13 may be configured to enable the plurality of sensors to be removably attached to the apparatus 1. The sensors may be removably attached to the apparatus 1 so that a first sensor can be attached to the apparatus 1 by a user. The user may then be able to remove the first sensor from the apparatus 1 and replace the first sensor with a second sensor. The second sensor may be a different type of sensor to the first sensor.

The receiving attachment portions 13 may be configured to enable a sensor to be positioned in close proximity to a coupling element 7. The plurality of attachment portions 11 may be configured to enable a sensor 2 to be positioned close enough to coupling element 7 to enable near field coupling between the sensor 2 and the coupling element 7.

In some examples the receiving attachment portions 13 and the sensors 2 may be configured so that when the sensors 2 are attached to the apparatus 1 the separation between the sensor 2 and the coupling element 7 is the same for each pairing of sensor 2 and coupling element 7. This may create a plurality of identical pairings of coupling elements 7 and receiving attachment portions 13.

In some examples the receiving attachment portion 13 may be configured to enable modules other than sensors to be removably attached to the apparatus 1. For example, the receiving attachment portion 13 may enable a light emitting element or display element to be removably attached to the apparatus 1.

The plurality of coupling elements 7 may comprise any means which enables the apparatus 1 to receive data. For example, the coupling elements 7 may comprise one or more antennas. The coupling element 7 may comprise reactive coupling elements such as inductive coils. The reactive coupling elements may be inductive or capacitive elements. The coupling elements 7 may enable the apparatus 1 to receive data from a sensor attached to the apparatus 1. In some embodiments the coupling elements 7 may enable the data to be received using a wireless communication link such as a near field communication link or any other suitable communication link. It is to be appreciated that in some embodiments the coupling elements 7 may enable data to be transmitted.

In the example illustrated in FIG. 1 the number of coupling elements 7 equals the number of receiving attachment portions 13. This may enable a plurality of sensors 2 to be attached to the apparatus 1 so that each of the sensors 2 has an established communication link with a different coupling element 7. In some examples the communication link may be a wireless communication link. In other examples a wired link or direct electrical connection may be used.

In some examples each of the plurality of coupling elements 7 may be identical. Each of the plurality of coupling elements 7 may have the same resonant frequency. Each of the plurality of coupling elements 7 may be configured to have the same coupling factor with a corresponding sensor 2.

The example apparatus of FIG. 1 also comprises a controller 4. The controller 4 provides means for controlling the apparatus 1. The controller 4 may be implemented using instructions that enable hardware functionality, for example, by using executable computer program instructions in a general-purpose or special-purpose processor that may be stored on a computer readable storage medium (disk, memory etc) to be executed by such a processor. The controller 4 may comprise a processor 3 and at least one memory 5.

The processor 3 is configured to read from and write to the memory 5. The processor 3 may also comprise an output interface via which data and/or commands are output by the processor 3 and an input interface via which data and/or commands are input to the processor 3.

The memory 5 is configured to store a computer program 9 comprising computer program instructions (computer program code) 11 that controls the operation of the apparatus 1 when loaded into the processor 3. The computer program instructions 11, of the computer program 9, provide the logic and routines that enables the apparatus 1 to perform the methods described below. The processor 3 by reading the memory 5 is able to load and execute the computer program 9.

The apparatus 1 therefore comprises: at least one processor 3; and at least one memory 5 including computer program code 11 the at least one memory 5 and the computer program code 11 configured to, with the at least one processor 3, cause the apparatus 1 at least to individually address each of the plurality of antennas 7 to obtain a reading from each of the plurality of sensors attached to the apparatus 1.

The computer program 9 may arrive at the apparatus 1 via any suitable delivery mechanism 21. The delivery mechanism 21 may comprise, for example, a non-transitory computer-readable storage medium 23, a computer program product, a memory device, a record medium such as a compact disc read-only memory (CD-ROM) or digital versatile disc (DVD), an article of manufacture that tangibly embodies the computer program 9. The delivery mechanism 21 may comprise a signal configured to reliably transfer the computer program 9. The apparatus 1 may propagate or transmit the computer program 9 as a computer data signal.

Although the memory 5 is illustrated as a single component in the example of FIG. 1 it may be implemented as one or more separate components some or all of which may be integrated/removable and/or may provide permanent/semi-permanent/dynamic/cached storage.

Although the processor 3 is illustrated as a single component in the example of FIG. 1 it may be implemented as one or more separate components some or all of which may be integrated/removable.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' refers to all of the following:
(a) hardware-only circuit implementations (such as implementations in only analog and/or digital circuitry) and
(b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and
(c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in server, a cellular network device, or other network device."

The example apparatus 1 illustrated in FIG. 1 comprises a housing 15. The plurality of coupling elements 7 and the controller 4 may be provided within the housing 15. The plurality of receiving attachment portions 13 may be provided on a surface of the housing 15 to enable the sensors 2 to be attached directly to the apparatus 1.

The plurality of coupling elements 7 may be provided close to the surface of the housing 15 to enable the sensors 2 to be provided in close proximity to the plurality of coupling elements 7. In some examples of the disclosure the distance between the surface of the housing 15 and each of the plurality of coupling elements 7 may be the same.

In some examples of the disclosure the housing 15 may be configured to enable the apparatus 1 to be worn by the user. For example the housing 15 may enable the apparatus 1 to be mounted on the body of the user. In such examples, the housing 15 may comprise a strap which may be worn around a wrist or other body part of the user. In other examples the housing 15 may comprise a lanyard which may enable the apparatus 1 to be worn around the neck of the user or any other suitable means.

Figure 2:
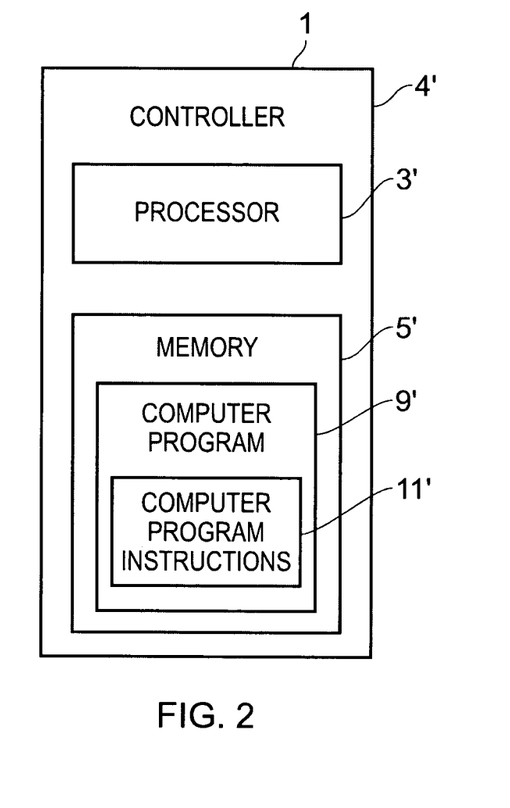
FIG. 2 illustrates an apparatus according to other examples of the disclosure.

FIG. 2 illustrates an apparatus 1' according to another embodiment of the disclosure. The apparatus 1' illustrated in FIG. 2 may be a chip or a chip-set. The apparatus 1' comprises at least one processor 3 and at least one memory 5 as described above in relation to FIG. 1.

Figure 3:
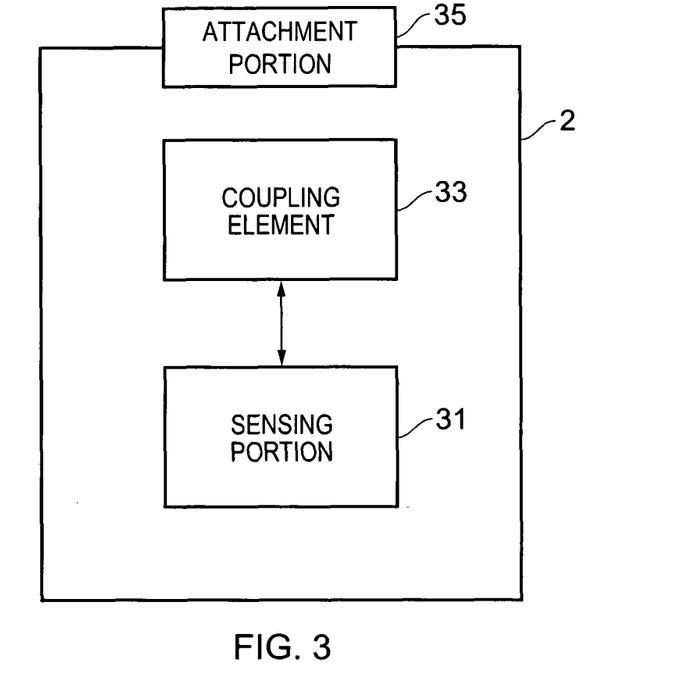
FIG. 3 illustrates a sensor according to examples of the disclosure.

FIG. 3 schematically illustrates a sensor 2 according to an example disclosure. The sensor 2 comprises a sensing portion 31, a coupling element 33 and an attachment portion 35.

The sensing portion 31 may comprise any means which may be configured to sense a parameter and provide a signal indicative of the sensed parameter. The signal indicative of the sensed parameter may be provided to the coupling element 33. The sensing portion 31 which is used may dependent on the parameter which is to be sensed. Different sensors 2 may be configured to sense different parameters and so different sensors 2 may have different types of sensing portions 31.

In some examples the sensing portion 31 may comprise at least one variable resistor sensor where the resistor has a resistance that varies with a sensed parameter. The sensing portion 31 may comprise at least one variable resistance sensor which may have a variable resistance that varies with, for example, presence of a specific chemical or biochemical molecule, incident light, humidity, temperature, stress or any other suitable parameter.

In some examples the sensing portion 31 may comprise at least one capacitive sensor where the capacitive sensor has a capacitance that varies with a sensed parameter. The sensing portion 31 may comprise at least one capacitive sensor which may have a capacitance that varies with, for example, presence of a specific chemical or biochemical molecule, incident light, humidity, temperature, stress or any other suitable parameter.

In some examples the sensing portion 31 may comprise both variable resistive sensors and capacitive sensors. It is to be appreciated that other transduction methods could be used in other examples such as surface acoustic waves, piezoelectric mechanism or thermocouples or any other suitable mechanism.

The coupling element 33 may comprise any means which enables the sensor 2 to transfer data. The coupling element 33 may comprise one or more antennas or reactive coupling elements. The reactive coupling elements may be inductive or capacitive elements. The coupling element 33 may enable the sensor 2 to transfer data to an apparatus 1 such as the apparatus illustrated in FIG. 1 and described above. In some examples the coupling element 33 may enable the data to be transferred using a wireless communication link such as a near field communication link or any other suitable communication link. In other examples the communication link may be a wired link or a direct electrical connection.

The attachment portion 35 may be configured to enable the sensor 2 to be removably attached to an apparatus 1 such as the apparatus 1 illustrated in FIG. 1 and described above. The attachment portion 35 may be configured to enable the sensor 2 to be removably attached to the apparatus 1 so that a first sensor 2 can be attached to the apparatus 1 by a user. The user may then be able to remove the first sensor 2 from the apparatus 1 and replace the first sensor 2 with a second sensor 2. The second sensor 2 may be a different type of sensor to the first sensor 2. For example, the first sensor 2 may be configured to sense a first parameter and the second sensor 2 may be configured to sense a second, different parameter.

The attachment portion 35 may comprise any means which may enable the sensor 2 to be removably attached to an apparatus 1 such as the apparatus illustrated in FIG. 1. For example the attachment portion 35 may comprise an adhesive portion which may be attached to a corresponding receiving attachment portion 13 of the apparatus 1. In other examples the receiving attachment portion 13 of the apparatus 1 may comprise a slot and the attachment portion 35 of the sensor 2 may comprise a portion sized and shaped to fit into the slot. It is to be appreciated that other attachment portions may be used in other examples.

In some examples the attachment portion 35 may be configured to enable the sensor 2 to be positioned in close proximity to a coupling element 7 of the apparatus 1.

Figure 4:
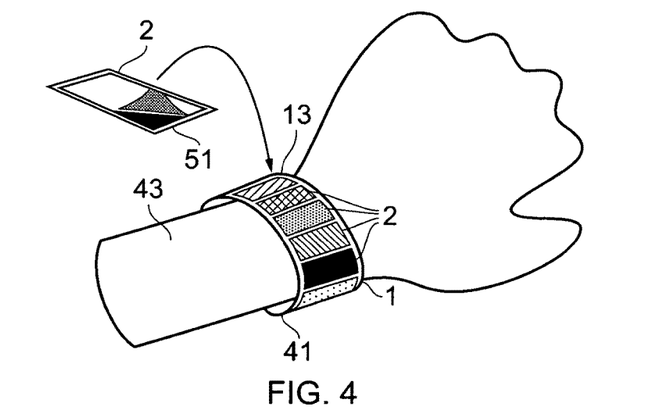
FIG. 4 illustrates an example apparatus in use.

FIG. 4 illustrates an example apparatus 1 in use. In FIG. 4 plurality of sensors 2 are attached to the apparatus 1 by the respective attachment portions 13, 35. It is to be appreciated that in some examples other modules, such as displays may be attached to the apparatus 1. In some examples each of the sensors 2 may be different. Each of the sensors 2 may be configured to be sensitive to a different parameter. The user may be able to select the types of sensors 2 which are to be used and attach these to the apparatus 1. This may enable the user to select which parameters are to be detected.

In this example the apparatus 1 comprises a strap 41 which is wrapped around the wrist 43 of the user. The strap 41 hold the apparatus 1 in a position close the skin of the user and enable at least a subset of the sensors 2 attached to the apparatus 1 to sense parameters relating to a physiological condition of the user of the apparatus 1. In other examples the strap 41 may be used to attach the apparatus 1 to a different part of the users body such as the chest or any other suitable part.

In this particular example the plurality of attachment portions 13 extend along the length of the strap 41 so that when the sensors 2 are attached to the attachment portions 13 the sensors 2 extend along the length of the strap 41. In the example of FIG. 4 the user is attaching a further sensor 2 to the apparatus 1. The further sensor 2 is provided on a carrier card 51. The carrier card 51 may provide a flat or substantially flat substrate which the sensor 2 may be attached to before the sensor 2 is attached to the apparatus 1. The carrier card 51 may protect the sensor 2 from damage before the sensor is attached to the apparatus 1. The carrier card 51 may protect the sensor 2 while it is being transported.

In some examples the carrier card 51 may also comprise a protective layer for the sensor 2. The protective layer may comprise an impermeable layer which may prevent the sensing portion 31 of the sensor 2 from being exposed to environmental parameters, such as humidity, which could affect the sensor 2 before it is attached to the apparatus 1.

In some examples the apparatus 1 may comprise an alignment portion which may be configured to enable a user align the sensor 2 on the apparatus 1. In some examples the alignment portion may comprise a visual indicator on the sensor 2 and the apparatus 1. The user may position the sensor 2 in the correction position and orientation by aligning a visual indication on the sensor 2 with a visual indication on the apparatus 1. In other examples the alignment portion may comprise the shape of the sensor 2. For example, the sensor 2 may be shaped so that it can only be attached to the apparatus 1 in a particular orientation. This may enable the user to position the sensors 2 on the apparatus 1 so that the coupling factor between each of the coupling elements 7 of the apparatus 1 and the coupling elements 33 of the sensor 2 is the same.

In some examples the sensor 2 may also comprise a portion which may be configured to provide a visual indication of a sensed parameter. For example a temperature sensor may comprise a portion which is configured to change color as the temperature changes. In such examples the visual indication may comprise thermochromic ink or polymer printed on the sensor 2 or any other suitable visual indicator.

The sensor 2 may be attached to the carrier card 51 using an adhesive portion. In the example of FIG. 4 the user removes the sensor 2 from the carrier card 51 by peeling the sensor 2 off the carrier card 51. The user can then use the adhesive portion of the sensor 2 to removably attach the sensor 2 to a receiving attachment portion 13 of the apparatus 1.

In some examples each of the receiving attachment portions 13 and corresponding coupling elements 7 of the apparatus 1 are identical. The user may be able to attach the sensors 2 to any of the available attachment portions 1 and the readings which are obtained from the sensor 2 would not be dependent on the attachment portion of the apparatus 1 which is selected.

Figure 5A:
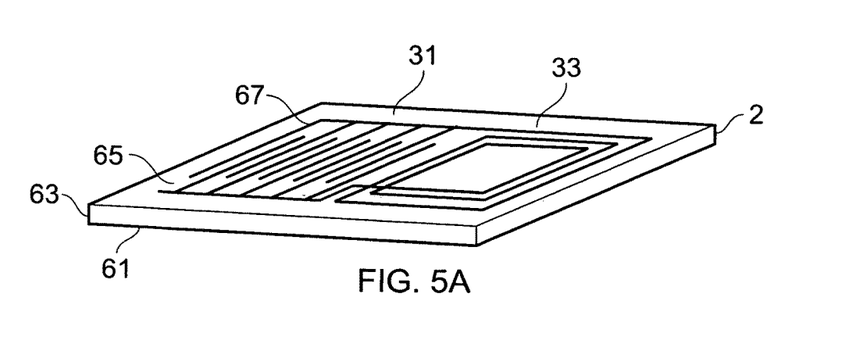
FIGS. 5A and 5B illustrate further details of example sensors.
Figure 5B:
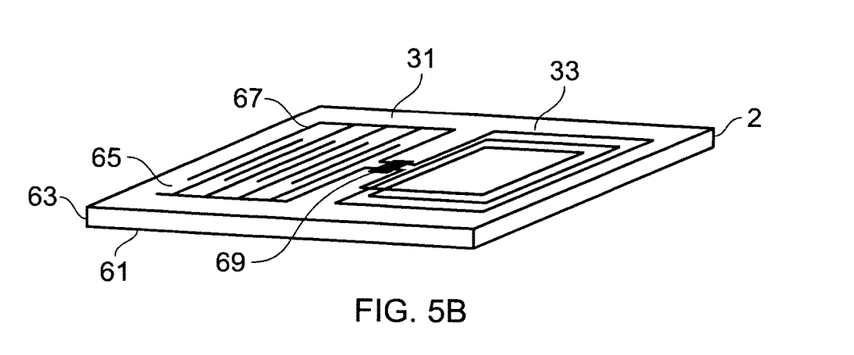

FIGS. 5A and 5B illustrate example sensors 2 in more detail.

In these embodiments the sensor 2 comprises a sensing portion 31 and an antenna 33 and an attachment portion 35 as described above in relation to FIG. 3.

The sensing portion 31 and the coupling element 33 may be provided on a substrate 63. The substrate 63 may comprise a flexible material which may enable the sensor 2 to be peeled off a carrier card 51 and attached to an apparatus 1. The substrate 63 may comprise a polymer such as Polyethylene Terephtalate (PET), Polyethylene Napthalate (PEN), or any other suitable material.

In the examples of FIGS. 5A and 5B the sensing portions 31 comprise a sensing material 65 and sense electrodes 67.

The sensing material 65 may comprise any material which may be configured to be sensitive to specific parameters. For example, the sensing material 65 may comprise any material which may be configured to be sensitive to environmental parameters such as temperature, light, humidity, biological or chemical molecules or any other suitable parameters. In some embodiments the parameters which are sensed by the sensing material 65 may comprise parameters relating to a physiological condition of the user of the apparatus 1. For example, the environmental parameters may include parameters relating to the physiological properties such as the conductivity of the user's skin, the temperature of the user's skin, the humidity of the user's skin, the pulse rate of the user or any other property such as the pH of the skin or sweat. The sensing material 65 which is used may depend on the parameter which is to be sensed.

The sensing material 65 used in the sensing portion 31 may have a capacitive or resistive transduction mechanism. If the sensing material 65 has a capacitive transduction mechanism then the presence of the sensed parameter may change the permittivity of the material. Similarly if the sensing material 65 has a resistive transduction mechanism then the presence of the sensed parameter may change the resistivity of the material. It is to be appreciated that other transduction mechanisms could be used in other examples.

The sensing electrodes 67 may be formed using conductive ink such as silver ink or any other suitable material. In the examples of FIGS. 5A and 5B the sensing electrodes 67 are provided in an interdigitated arrangement. The electrodes 67 may be arranged in parallel with the sensing material 65.

It is to be appreciated that in other examples different arrangements of electrodes and sensing material 65 may be used.

In the examples of FIGS. 5A and 5B the coupling element 33 may be configured to enable the sensor 2 to be inductively coupled to coupling element 7 of an apparatus 1 when the sensor 2 is attached to a receiving attachment portion 13 of the apparatus 1. The coupling element 33 may be configured to enable near field coupling between the sensor 2 and a coupling element 7 of an apparatus 1. In some examples the coupling element 7 may comprise a coil.

The coupling element 33 is coupled to the sensing portion 31 so that the detection of a parameter by the sensing portion 31 changes the frequency response of the coupling element 33. In some examples the coupling element 33 may be coupled to the sensing portion 31 so that changes in the reactance of the sensing portion 31 change the frequency response of the coupling element 33.

In the examples of FIGS. 5A and 5B the attachment portion 35 comprises an adhesive layer 61. In the particular examples of FIGS. 5A and 5B the adhesive layer is provided 61 on the underside of the substrate 63. The adhesive layer 61 may enable the sensor 2 to be removably attached to an apparatus 1. The adhesive layer 61 may also enable the sensor 2 to be attached to a carrier card 51 such as the card illustrated in FIG. 4.

In the example of FIG. 5A the sensing portion 31 is connected in parallel to the coupling element 33. A change in the reactance of the sensing portion 31 causes a change in the resonant frequency of the coupling element 7 and the response which would be provided to a reader coupling element 7 of an apparatus 1.

In the example of FIG. 5B the sensor 2 comprises a microchip 69. The microchip 69 may be connected between the sensing portion 31 and the antenna 33. The microchip 69 may be powered by absorbing energy from the field provided by the reading coupling elements 7. The microchip 69 may be configured to digitally encode the signal provided by the sensing portion 31 before it is provided to the antenna 33. In such examples the antenna 33 may be configured to transmit a digitally encoded signal from the sensor 2 to the apparatus 1. The digitally encoded signal may comprise data indicative of the sensed parameter. In some examples the digitally encoded data may also comprise identification information relating to the sensor 2. In some examples the microchip 69 may comprise one or more memories which may be configured to store information such as calibration data or threshold settings. This information may be stored in the memory during manufacture of the sensor 2. The information may be read by the reading coupling element 7.

The sensors 2 may be produced using roll-to-roll printing or any other suitable manufacturing process. Once the electrodes 67 and coupling elements 33 have been printed the sensing material 65 may be added. For example, a humidity sensor may be obtained by adding a humidity-sensitive polymer coating onto electrodes which are in parallel with a printed inductive coil. This may enable the sensors 2 to be manufactured cheaply and easily.

Figure 6:
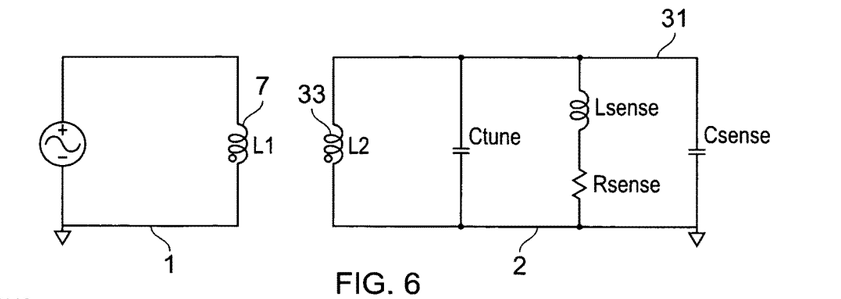
FIG. 6 illustrates an equivalent circuit of a sensor and apparatus.

FIG. 6 illustrates an equivalent circuit of a sensor 2 and apparatus 1 as described above.

The apparatus 1 comprises a signal generator and generates a sine wave signal which is transmitted by the coupling element 7 of the apparatus 1.

The coupling element 7 of the apparatus 1 is inductively coupled to the antenna 33 of the sensor 2. The sensing portion 31 of the sensor 2 is equivalent to a tuning circuit comprising a resistor $R_{sense}$ and an inductor $L_{sense}$ in parallel with a capacitor $C_{sense}$. A tuning capacitor $C_{tune}$ may be provided to enable each sensor 2 to enable the sensors 2 to be tuned have the same resonant frequency at manufacture. The tuning capacitor may ensure that the resonant frequency of the sensor 2 is matched to the resonant frequency of the apparatus 1.

The reactance of the components of the tuning circuit may vary in dependence on the parameters sensed by the sensing portion 31. The variation of the reactance of the components 31 of the sensing portion 31 causes a variation in the frequency response of the sensor 2.

The apparatus 1 generates a voltage sine wave. In some examples the generated sine wave may have a single frequency. In other examples the sine wave may be provided over a range of frequencies.

The sensor antenna 33 backscatters the generated sine wave. The modulation in the backscattered signal depends on the reactance of the sensor 2.

Each sensor 2 may be calibrated to have the same resonant frequency at manufacture. When the sensing portion 31 senses a parameter this changes the reactance of the sensor 2 and so changes the resonant frequency of the sensor 2. This results in a change of the backscattered signal. The antenna 5 of the apparatus 1 may be configured to detect a change in the backscattered signal.

The apparatus 1 may be configured to detect a change in the backscattered signal. The apparatus 1 may be configured to detect a threshold value for a change in the backscattered signal. The threshold value may correspond to a threshold value of a parameter which is to be sensed by the sensing portion 31.

Figure 7A:
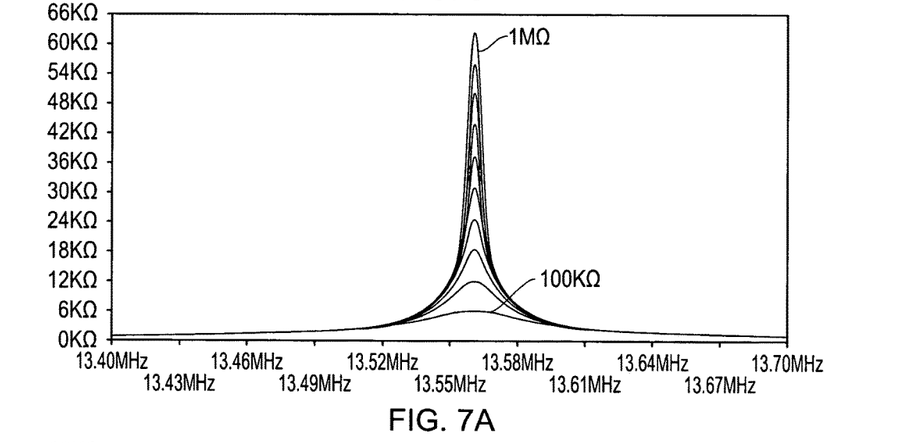
FIGS. 7A and 7B illustrate the frequency response of a sensor according to examples of the disclosure.
Figure 7B:
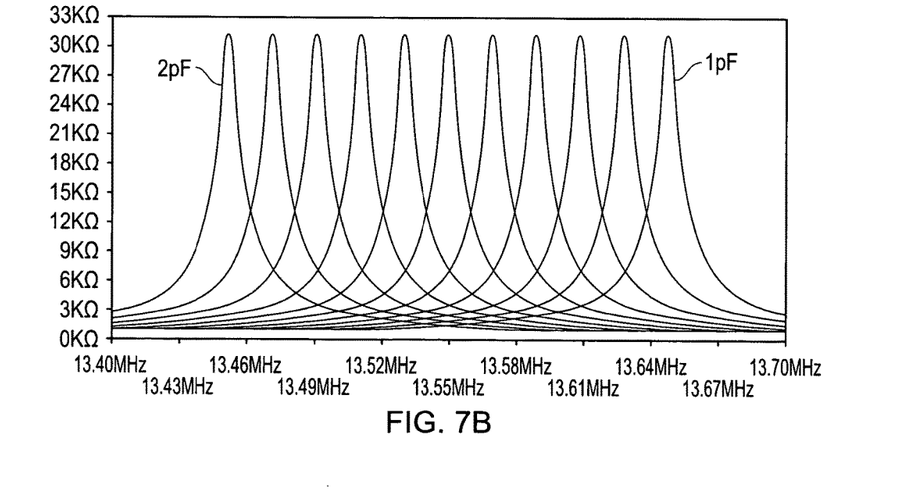

FIGS. 7A and 7B illustrate the frequency response of the impedance of the coupling element 33 of the apparatus 1 according to examples of the disclosure.

FIG. 7A illustrates the change in the frequency response as the resistance of the sensor 2 changes. In this example the resistance of $R_{sense}$ changes from 100 KΩ to 1 MΩ.

In this example the resonant frequency of the sensor 2 does not change as the inductance and reactance don't change. However, as $R_{sense}$ increases the resonance of the sensor 2 is damped more strongly. The amplitude of the backscattered signal is dependent on the damping of the resonance of the sensor 2. When the sensing portion 31 detects a parameter to be changed this may change the value of $R_{sense}$ which will change the damping of the resonance of the sensor and change the amplitude of the backscattered signal so that the reader shows a different response.

FIG. 7B illustrates the change in the frequency response as the capacitance of the sensor 2 changes. In this example the capacitance of $C_{sense}$ changes from 1 pF to 2 pF.

In this example, changing the capacitance changes the resonant frequency of the sensor 2. This changes the amplitude of the back scattered signal for a given frequency and so changes the response detected by the reading coupling element 33.

Examples where the readings are obtained over a range of frequencies may enable more information to be obtained from the sensor 2. The information may comprise the resonant and anti-resonant frequencies of the real and imaginary impedance as well as the impedance magnitude. This may enable the apparatus 1 to be more sensitive to a particular parameter.

Figure 8:
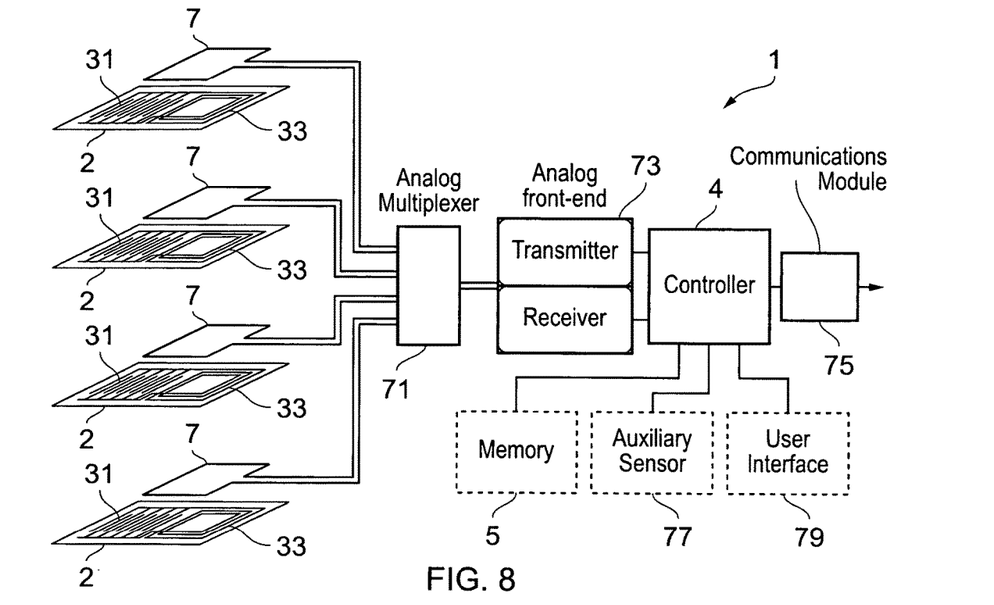
FIG. 8 schematically illustrates an apparatus and plurality of sensors according to another example.

FIG. 8 schematically illustrates an apparatus 1 and plurality of sensors 2 according to another example. In this example the apparatus 1 is illustrated as comprising four coupling elements 7 and four corresponding sensors 2 are provided.

The sensors 2 in FIG. 8 may be sensors 2 as illustrated in FIG. 5A or 5B, comprising sensing portion 31 and coupling elements 33 as described above.

The respective sensors 2 are arranged so that the coupling elements 33 of the sensors 2 is aligned with a corresponding antenna 7 of the apparatus 1. Each of the plurality of coupling elements 7 may be identical. The receiving attachment portions 13 may be configured so that the coupling factor between each pairing of antenna 7 and sensor 2 is the same.

In some examples the coupling factor may be dependent on the geometrical arrangement of the two coupling elements 7, 33. For example, in examples where near field communication is used the coupling factor may be dependent on the separation between the coupling elements 7, 33, the size of the coupling elements 7, 33 and their relative orientation. To ensure that the coupling factor is the same the separation between the coupling elements 7 of the apparatus 1 and the coupling element 33 of the sensor 2 may be the same for each pairing of coupling element 7 and sensor 2. The apparatus 1 may comprise visual indicators to ensure that the sensor 2 is attached to the apparatus 1 in the right way to ensure that the relative orientation of the coupling elements 7, 33, is the same for each pair of coupling elements 7, 33. This may enable any of the available receiving attachment portions 13 of the apparatus 1 to be used to attach a sensor 2 as the reading obtained would be the same for any of the identical coupling elements 7.

The attachment portions 13, 35 may be configured to enable the plurality of sensors 2 to be positioned in close proximity to the coupling elements 7 of the apparatus 1. The attachment portions 13, 35 may be configured to enable the plurality of sensors 2 to be arranged to optimize the coupling between the coupling elements 33 of the sensor 2 and the coupling element 7 of the apparatus 1. This may enable small coupling elements 7 to be used with low power consumption. This may also reduce the interference between adjacent or nearby coupling elements 7.

The apparatus 1 illustrated in FIG. 8 also comprises an analog multiplexer 71, an analog front end 73, a controller 4 and a communications module 75.

The analog multiplexer 71 is configured to provide the signals obtained from each of the plurality of coupling elements 7 to the analog front end 73. The analog multiplexer 71 reduces the number of input and output connections to the controller 4

The analog front end 73 converts the received signal to a digital signal and provides the converted signal to the controller 4.

The controller 4 is configured to individually address each of the plurality of antennas 7 and obtain a reading from each of the sensors 2 indicative of the sensed parameters. The controller 4 may be configured to write to and read from a memory 5 as described above.

In some examples the controller 4 may be configured to perform functions such as calibrate the sensors 2, convert the data obtained from the sensors 2 into data which may be transmitted using the communications module or encrypt the data before it is transmitted or any other suitable function.

The controller 4 may be configured to control the apparatus 1 so that the data obtained from the sensor 2 is only transmitted by the communications module 75 when a threshold is exceeded. This may reduce the power consumption of the apparatus 1. In other examples the controller 4 may be configured to control 4 the apparatus 1 so that the data obtained from the sensor 2 is transmitted at given time intervals.

In the example of FIG. 8 the apparatus 1 also comprises a communications module 75. The communications module 75 may enable the apparatus 1 to provide the readings obtained from the plurality of sensors 2 to another apparatus.

In some examples the communications module 75 may be configured to enable the apparatus 1 to communicate in a wireless communications network. The wireless communications network may be a low power radio frequency network such as a Bluetooth network or any other suitable type of network.

In the particular example of FIG. 8 the apparatus 1 also comprises an auxiliary sensor 77 and a user interface 79.

In some examples a plurality of auxiliary sensors 77 may be provided. The auxiliary sensors 77 may be permanently attached to the apparatus 1 or attached to the apparatus 1 in such a way that they cannot be easily removed by a user of the apparatus 1. The auxiliary sensors 77 may be configured to detect parameters which may be used as references for other sensors 2. For example the auxiliary sensors 77 may detect parameters such as temperature or humidity.

The user interface 79 may comprise any means which enables user to input information to the apparatus 1. The input information may enable the user to control the apparatus 1. For example the input information may enable the user to specify which parameters are to be sensed or set threshold parameters or make any other suitable control input.

In some examples the user interface 79 may comprise means for providing information to a user such as a display or an audio output means. The information which is provided to the user may comprise any suitable information such as an indication of data which has been obtained by the sensors 2 or information relating to the status of the apparatus 1 such as the power levels available in the apparatus 1.

In some examples the apparatus 1 may be configured to be turned on and off by a user. For example, if the apparatus 1 is configured to monitor the physiological conditions of a user during physical activity the user may switch the apparatus 1 on when they start the activity and turn the apparatus 1 off when they complete the activity. In other examples the apparatus 1 may be configured to switch between an active and inactive mode at pre-determined intervals or in response to an external stimulus such as movement.

Figure 9:
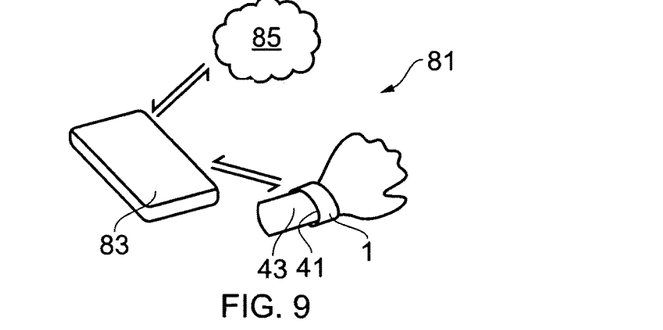
FIG. 9 illustrates a communications system comprising an apparatus according to examples of the disclosure.

FIG. 9 illustrates a communications system 81 comprising an apparatus 1 as described above. In this example the communications system 81 comprises a mobile communications device 83 such as a mobile telephone or tablet computer. The communications module 75 of the apparatus 1 may be configured to communicate with the mobile communications device 83. The apparatus 1 may be configured to provide the data obtained from the plurality of sensors 2 to the mobile communications device 83.

In the example of FIG. 9 the communications device 83 may be configured to communicate with a network 85. The communications device 83 may be configured to transmit the data received from the apparatus 1 to the network 85. The network 85 may be for example a cloud network, the Internet, a cellular communications network or any other suitable network.

Figure 10:
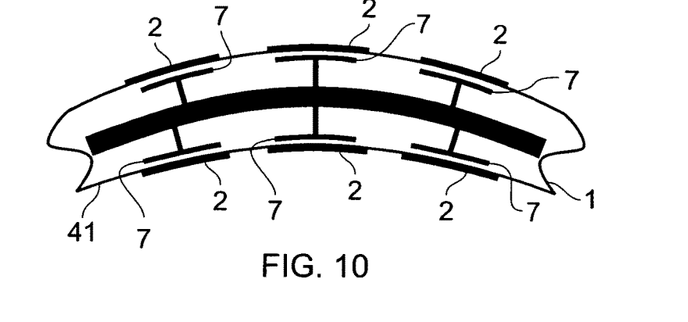
FIG. 10 illustrates a cross section through an apparatus 1 according to another example.

FIG. 10 illustrates a cross section through an apparatus 1 according to another example. In this example the apparatus 1 comprises a strap 41 which may enable the apparatus 1 to be attached to the body of the user.

The strap 41 may comprise attachment portions 13 on either side of the strap 41 so that the sensors 2 can be attached on either side of the strap 41. The sensors 2 which are attached on the underside of the strap 41 may be positioned adjacent to the skin of the user when the apparatus 1 is attached to the user. These sensors 2 may be configured to detect parameters relating to physiological conditions. The sensors 2 on the outer surface of the strap 43 may not be in contact with the skin of the user when the apparatus 1 is attached to a user. The sensors 2 on the outer surface may be configured to detect other parameters, such as environmental parameters.

The examples described above provide an apparatus 1 which may be configured by a user to enable a variety of different parameters to be sensed. As the user may be able to removably attach the sensors 2 to the apparatus 1 the user may be able to select which sensors 2 to use. For example a user may be able to buy and select sensors 2 from a range of different types of available sensors 2. This may enable the user to personalize the apparatus 2 and may enable the user to optimize the apparatus 1 for a specific purpose.

In some examples the sensors 2 may be disposable so the user of the apparatus 1 may be able to change the sensor 2 whenever they want or need to. This may be particularly useful for sensors 2 which may degrade over time such chemical or biological sensors.

In the above description coupled may mean operationally coupled and any number or combination of intervening elements can exist (including no intervening elements) between coupled components.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class.

Although embodiments of the present invention have been described in the preceding paragraphs with reference to various examples, it should be appreciated that modifications to the examples given can be made without departing from the scope of the invention as claimed. For example, in FIG. 5 the sensing material 35 is provided on electrodes 67. In other examples the sensing material 65 may be placed directly onto the coupling element 33.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. An apparatus comprising:
a plurality of coupling elements;
a plurality of attachment portions configured to enable a plurality of sensors to be removably attached to the apparatus, where the coupling elements are configured to form wireless communication links with the sensors when the sensors are attached to the attachment portions;
at least one processor; and
at least one memory including computer program instructions;

wherein the at least one memory and the computer program instructions are configured to, with the at least one processor, enable the apparatus to individually address each of the plurality of coupling elements to obtain a reading from each of the plurality of sensors, attached to the apparatus, via the wireless communication links.

2. An apparatus as claimed in claim 1 wherein each of the plurality of coupling elements is identical.

3. An apparatus as claimed in claim 1 wherein at least one of the coupling elements comprises an antenna.

4. An apparatus as claimed in claim 3 wherein the plurality of attachment portions are configured so that the separation between the sensor and the antenna is the same for each pairing of sensor and antenna.

5. An apparatus as claimed in claim 1 wherein the plurality of attachment portions are configured to enable a user of the apparatus to remove and replace the plurality of sensors.

6. An apparatus as claimed in claim 1 wherein the plurality of attachment portions are configured to enable a respective one of the sensors to be positioned in close proximity to a respective one of the coupling elements.

7. An apparatus as claimed in claim 1 wherein the plurality of attachment portions are configured to enable at least one of the sensors to be positioned close enough to a respective one of the coupling elements to enable near field coupling between the sensor and the coupling element.

8. An apparatus as claimed in claim 1 wherein the plurality of attachment portions comprises means for coupling to a corresponding attachment portion of a sensor.

9. An apparatus as claimed in claim 1 wherein the plurality of attachment portions comprises a portion configured to receive an adhesive portion of at least one of the sensors.

10. An apparatus as claimed in claim 1 wherein the apparatus is configured to be worn by a user.

11. An apparatus as claimed in claim 1 wherein the apparatus comprises a strap configured to enable the apparatus to be attached to a user's body.

12. An apparatus as claimed in claim 11 wherein a first subset of the plurality of sensors are provided on a first side of the strap and a second subset of the plurality of sensors are provided on a second side of the strap.

13. An apparatus as claimed in claim 12 wherein the apparatus is configured so that, when the apparatus is attached to the user's body, the second subset of sensors is positioned to be adjacent to the skin of the user's body.

14. An apparatus as claimed in claim 1 wherein the apparatus comprises a communications module configured to enable the apparatus to communicate with another apparatus.

15. A sensor configured to be attached to an apparatus as claimed in claim 1.

16. A sensor comprising:
a sensing portion;
at least one coupling element connected to the sensing portion such that a detection of a parameter by the sensing portion changes a frequency response of the at least one coupling element, where the at least one coupling element is configured to form at least one wireless communication link to an apparatus; and
an attachment portion configured to enable the sensor to be removably attached to the apparatus to enable the at least one coupling element to transfer data to the apparatus;
wherein the sensor is configured to transfer data to the apparatus both before and after the change in frequency response.

17. A sensor as claimed in claim 16 wherein the sensor portion is configured to sense the parameter and to provide a signal indicative of the sensed parameter to the coupling element.

18. A sensor as claimed in claim 16 wherein the coupling element comprises an antenna.

19. A method comprising:
removably attaching at least one sensor to an apparatus wherein the apparatus comprises:
a plurality of coupling elements; a plurality of attachment portions configured to enable the at least one sensor to be removably attached to the apparatus, where the coupling elements are configured to form wireless communication links with the sensor(s) when the sensor(s) are attached to the attachment portions; at least one processor; and at least one memory including computer program instructions wherein the at least one memory and the computer program instructions are configured to, with the at least one processor, enable the apparatus to individually address one of the coupling elements to obtain a reading from the at least one sensor, attached to the apparatus, via the wireless communication links; and
the at least one sensor comprises: a sensing portion; a sensing antenna connected to the sensing portion such that a detection of a parameter by the sensing portion changes a frequency response of the sensing antenna, where the sensing antenna is configured to form a wireless communication link from the at least one sensor to the apparatus; and an attachment portion configured to enable the sensor to be removably attached to the apparatus.

20. A method comprising.:
removing a first sensor from an apparatus and replacing the first sensor with a second sensor, wherein the apparatus comprises:
a plurality, of coupling antennas; a plurality of attachment portions configured to enable at least the first sensor to be removably attached to the apparatus, where at least one of the coupling antennas is configured to form a wireless communication link with each sensor when the sensor is attached to the apparatus; at least one processor; and at least one memory including computer program instructions wherein the at least one memory and the computer program instructions are configured to, with the at least one processor, enable the apparatus to individually address at least one of the coupling antennas to obtain a reading from each sensor attached to the apparatus via the wireless communication link; and
the sensors comprise: a sensing portion; a sensing coupling element configured to form the wireless communication link; and an attachment portion configured to enable the sensors to be removably attached to the apparatus.

* * * * *